United States Patent
Bell et al.

(10) Patent No.: US 7,024,918 B2
(45) Date of Patent: Apr. 11, 2006

(54) APPARATUS AND METHODS FOR DYNAMICALLY PRESSURE TESTING AN ARTICLE

(75) Inventors: Andrew Bell, Carson City, NV (US); Christopher McMillen, Carson City, NV (US)

(73) Assignee: General Electric Company, Schenectady, NY (US)

( * ) Notice: Subject to any disclaimer, the term of this patent is extended or adjusted under 35 U.S.C. 154(b) by 211 days.

(21) Appl. No.: 10/780,698

(22) Filed: Feb. 19, 2004

(65) Prior Publication Data

US 2005/0183493 A1    Aug. 25, 2005

(51) Int. Cl.
*G01M 3/02*    (2006.01)

(52) U.S. Cl. .......................................................... 73/37
(58) Field of Classification Search .................... 73/37, 73/1.57, 1.71, 655
See application file for complete search history.

(56) References Cited

U.S. PATENT DOCUMENTS

| | | | | |
|---|---|---|---|---|
| 4,419,881 A | * | 12/1983 | Gentiluomo | 73/37 |
| 4,499,751 A | * | 2/1985 | Riggs | 73/1.67 |
| 5,665,919 A | * | 9/1997 | Woyski et al. | 73/665 |
| 5,677,480 A | * | 10/1997 | Liyanage et al. | 73/46 |
| 6,694,803 B1 | * | 2/2004 | Klik et al. | 73/37 |

OTHER PUBLICATIONS

Jan Hjelmgren Dynamic Measurement of Pressure—A Literature Survey—SP Swedish National Testing and Research Institute—SP Measurement Technology—Sp Report 2002: 34.

* cited by examiner

*Primary Examiner*—Hezron Williams
(74) *Attorney, Agent, or Firm*—Nixon & Vanderhye, P.C.

(57) ABSTRACT

The dynamic pressure tester includes a first cylinder and a first piston movable relative to the cylinder. The piston may have one or more weights applied thereto. The cylinder is vibrated by a shaker table and pressure pulses in the fluid are transmitted to a stationary housing and to a second piston in the housing. The opposite side of the piston contacts a corrosive or caustic fluid also in contact with the sensor face of an article being tested. The pressure pulses are transmitted by the second piston and corrosive fluid to the sensor face, enabling dynamic pressure testing in the corrosive fluid.

17 Claims, 4 Drawing Sheets

APPARATUS AND METHODS FOR DYNAMICALLY PRESSURE TESTING AN ARTICLE

The present invention relates to apparatus and methods for dynamically pressure testing an article and particularly relates to testing apparatus and methods for simulating dynamic pressure on an article exposed to caustic or corrosive fluids in practical applications of the article.

BACKGROUND OF THE INVENTION

Dynamic pressure testing of articles, for example, pressure transducers for use in various applications is well known. Dynamic pressure testing is typically used to test the longevity of an article, e.g., a pressure transducer when subjected to a plurality of time dependent cycles. Many and different types of dynamic pressure testing apparatus have been utilized. For example, shock tube testing provides two sections of a tubing separated by a thin diaphragm. When a differential pressure is applied to the tube sections and the diaphragm ruptures, a resulting pressure shock occurs. Disadvantages of shock tube dynamic pressure testing include a complexity of and difficulty for setting up the test, is limited to one cycle only, cannot use liquid fluid media during testing and the shock wave raises the gas temperature. Shockless pressure step generators use a quick opening valve to generate dynamic pressure pulses. Generators of this type, however, are limited mechanically by the opening of the valve and are unable to reach high frequency pulses, i.e., cycles per second. Pulse generators typically employ a mass dropped onto a piston in contact with an incompressible fluid contained within a fixed volume. Generators of this type, however, are limited to single step response, i.e., one cycle. There are also shaker base systems which utilize a liquid filled tube mounted on an armature of a shaker to produce dynamic pressure. Shaker base systems, however, are generally cumbersome, require heavy duty shakers for large pressure displacements, and have their own governing maximum operating temperatures.

Pistonphones utilize a piston-in-cylinder to produce a sinusoidal pressure variation. While devices of this type are typically used with acoustic sensors such as microphones, pistonphones are limited to low frequencies and amplitudes. Finally, servo-valves generally use hydraulic systems to control dynamic components. Pressure is generated by an external pump and is dynamically controlled by applying a biased alternating signal to the servo-valve. This signal moves a mechanical member inside the servo-valve, in turn directing working fluid through various ports and controlling a shuttle valve. The end result is a dynamic pressure signal at the output.

Oftentimes, these dynamic pressure systems cannot meet amplitude and frequency requirements for many applications. Further, many articles are subjected to caustic or corrosive fluids in use. The combined stresses caused by the caustic or corrosive fluids as well as the pressure variations to which the article is subjected in use are stresses not typically accounted for in prior dynamic pressure testing systems. There is also a need in certain applications for a very substantial number of pressure cycles in a short period of time, e.g., one billion cycles in 40 days or less, to insure the adequacy of the dynamic pressure testing.

BRIEF DESCRIPTION OF THE INVENTION

In accordance with an aspect of the present invention, there is provided a dynamic pressure testing apparatus and methods of dynamic pressure testing wherein the testing may be conducted at a significant range of frequencies, particularly high frequencies, with the article undergoing tests also being simultaneously subjected to caustic or corrosive fluids and the stresses caused thereby. In a preferred embodiment, a first cylinder with a piston slidable relative thereto are mounted on a shaker table or other suitable vibration generator whereby pressure pulses are generated in a first fluid in contact with the piston and cylinder. A second stationary housing or cylinder lies in fluid communication with the first fluid and includes a piston movable relative to the stationary housing or cylinder in response to the pressure pulses generated in the first fluid. The article undergoing testing lies in communication with a second fluid, e.g., a caustic or corrosive fluid also in communication with the second piston whereby the pressure pulses generated by the first fluid are transmitted via the second piston and second fluid to the article undergoing testing. With the article in contact with the caustic or corrosive second fluid and being subjected to the pressure pulses of the second fluid, the dynamic pressure testing may proceed at selected frequencies and amplitudes and temperatures limited only by the material of the testing apparatus. Moreover, by varying the mass of the first piston, e.g., by adding or removing mass to the first piston, the amplitudes and resonant frequencies of the generated pressure pulses can be varied as desired. For example, pressures can be generated with this test set-up in a range of 20–200 p.s.i. or higher with frequencies between about 100 Hz to about 400 Hz. A set-up of this type enables dynamic pressure testing using corrosive fluids over a large number of cycles in a limited time frame, e.g., one billion cycles in a matter of weeks and at desired resonant frequencies.

In a preferred embodiment according to the present invention, there is provided apparatus for dynamically pressure testing an article comprising a first cylinder containing a first fluid; a first piston in contact with the first fluid and movable within the first cylinder; a shaker table mounting the first cylinder and the first piston for vibrating the first cylinder and first piston and generating pressure pulses in the first fluid; a second fluid cylinder in communication with the first fluid, the second cylinder and a second piston movably carried by the second cylinder being mounted independently of the shaker table, the second piston in contact with the first fluid on one side thereof enabling the generated pressure pulses to vibrate the second piston; and a second fluid in the second cylinder in contact with the second piston on an opposite side thereof from the one side for receiving pressure pulses generated by the vibratory movement of the second piston and transmitting the second pressure pulses to an article undergoing dynamic pressure testing in contact with the second fluid.

In a preferred embodiment according to the present invention, there is provided apparatus for dynamically pressure testing an article comprising a first cylinder containing a first fluid; a first piston in contact with the first fluid and movable within the first cylinder; means for vibrating the first cylinder and the first piston to generate pressure pulses in the first fluid; a second fluid cylinder in communication with the first fluid, the second cylinder and a second piston movably carried by the second cylinder being mounted independently of the vibrating means, the second piston in contact with the first fluid on one side thereof, enabling the generated pressure pulses to vibrate the second piston; and a second fluid in the second cylinder in contact with the second piston on an opposite side thereof from the one side for receiving pressure pulses generated by the vibratory movement of the second piston and transmitting the second pressure pulses to an article undergoing dynamic pressure testing in contact with the second fluid.

In a preferred embodiment according to the present invention, there is provided apparatus

DETAILED DESCRIPTION OF THE INVENTION

Figure 1:
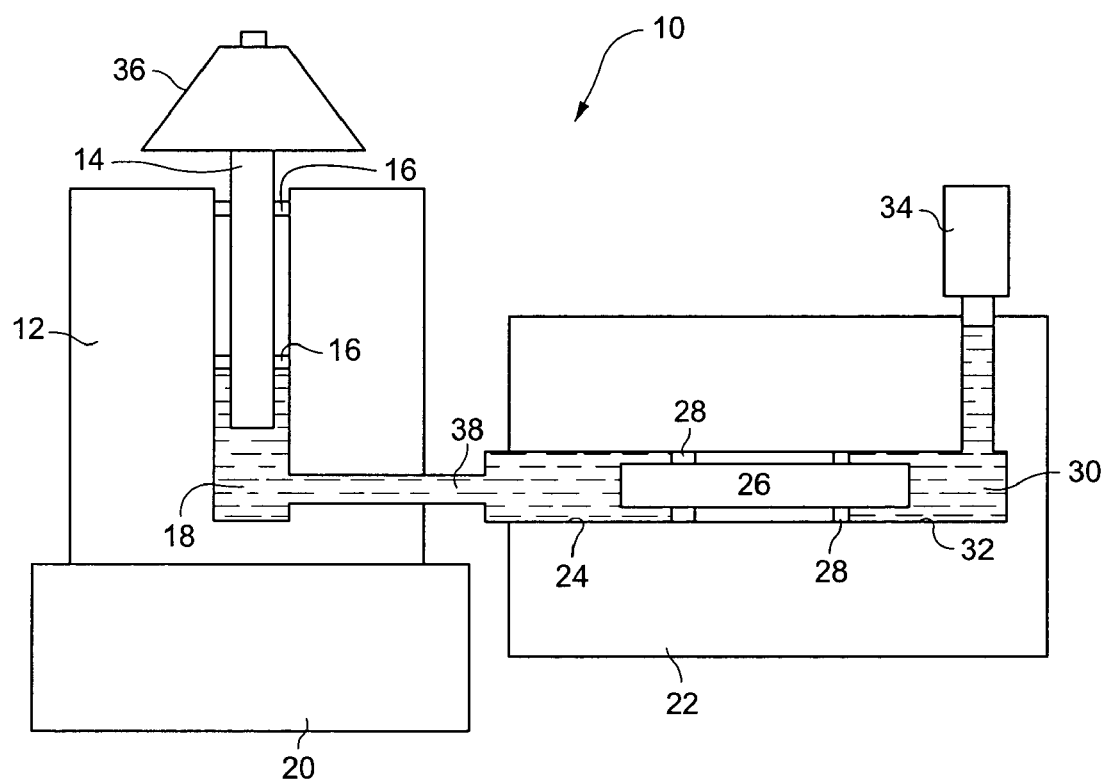
FIG. 1 is a schematic illustration of a dynamic pressure testing apparatus in accordance with a preferred aspect of the present invention.

Referring now to the drawings, particularly to FIG. 1, there is schematically illustrated a dynamic pressure testing apparatus in accordance with a preferred aspect of the present invention and generally designated 10. Apparatus 10 includes a fluid cylinder 12 and a piston 14, the cylinder 12 and piston 14 being oriented vertically. As illustrated, piston 14 is sealed within the cylinder 12 by seals 16 and a fluid 18 is disposed in the cylinder 12 below piston 14. The cylinder 12 is preferably disposed on a shaker table 20. Shaker table 20 may comprise a conventional shaker table, e.g., a shaker table identified as M&B Dynamics Cal 50, and preferably vibrates in a vertically oriented direction, enabling vibration of the cylinder 12 secured to the shaker table. It will be appreciated that any other suitable conventional apparatus for generating vibration may be used in lieu of a shaker table.

Apparatus 10 also includes a housing 22 carrying or forming a part of a second cylinder 24. A second piston 26 is also carried by cylinder 24. Piston 26 is sealed by seals 28 to the walls of cylinder 24 and lies in contact at one end with the fluid 18. The opposite end of piston 26 lies in contact with a fluid 30 in a chamber 32 within cylinder 24. Fluid 30 may be a caustic or corrosive fluid. As such, cylinder 24 and piston 26 and seals 28 are constructed from materials with the caustic fluid 30 media compatibility. At the opposite end of chamber 32 from piston 26 is the article 34 undergoing test. The article 34 is preferably secured to the housing 22. An example of an article 32 is a pressure transducer for measuring pressures in a caustic environment.

One or more discrete masses or weights 36 may be disposed on the upper end, i.e., an exposed end of the piston 14 to weight the piston depending upon the amplitude and frequency of the pressure pulses desired to be generated. It will be appreciated that by operating the shaker table 20 in a vertical vibratory mode or at least to have a vertical vibratory component, the cylinder 12 and weighted piston 14 generate vibratory pressure pulses in fluid 18. The vibratory pulses are transmitted to the fixed housing 22 via a semi-rigid connection 38 and serve to vibrate piston 26 within housing 22. The vibration of piston 26 within cylinder 22 is transmitted through the caustic or corrosive fluid 30 to the sensing face of the article undergoing testing, e.g., a pressure transducer.

Figure 2:
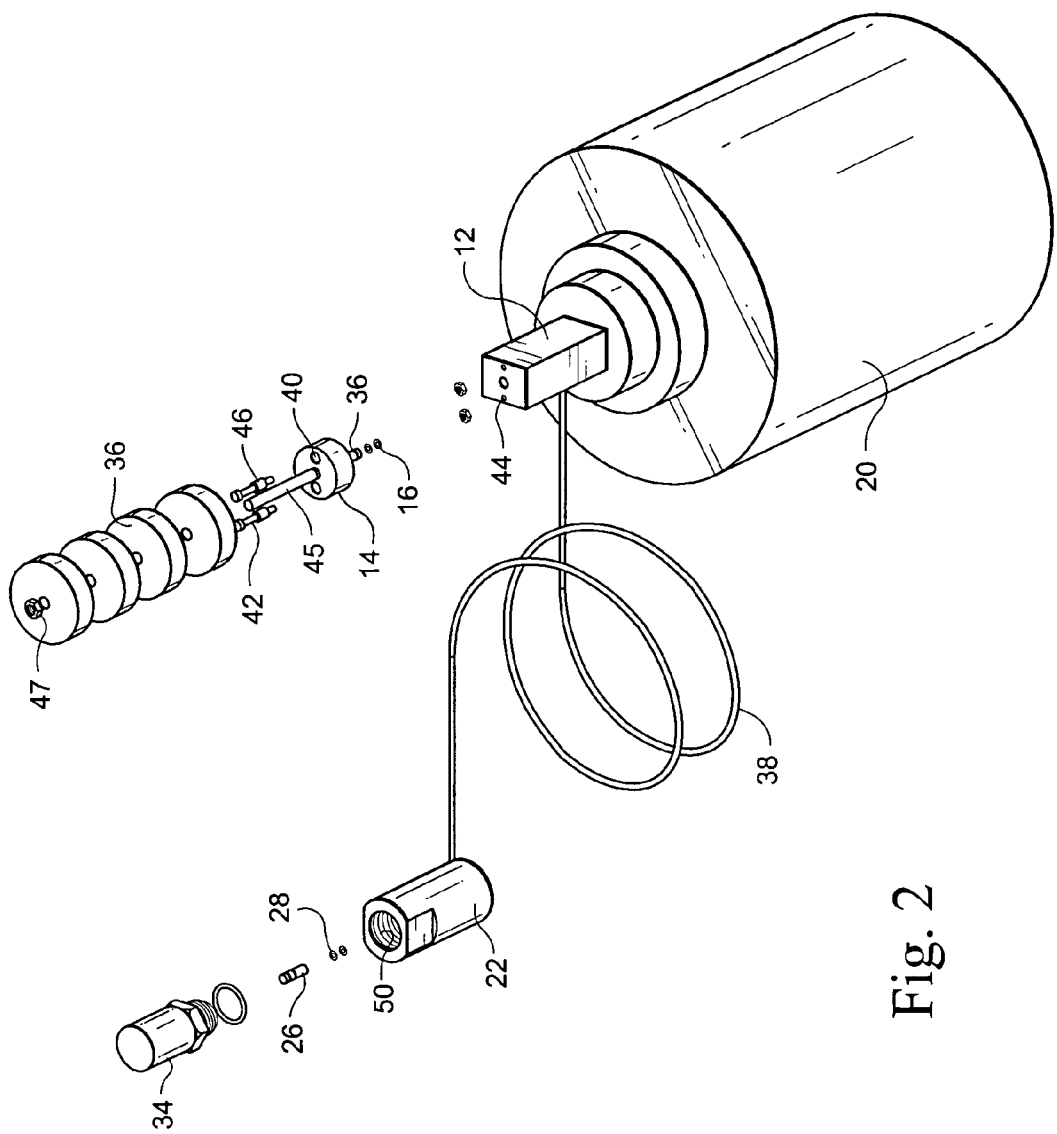
FIG. 2 is a perspective view of a dynamic pressure testing apparatus.
Figure 3:
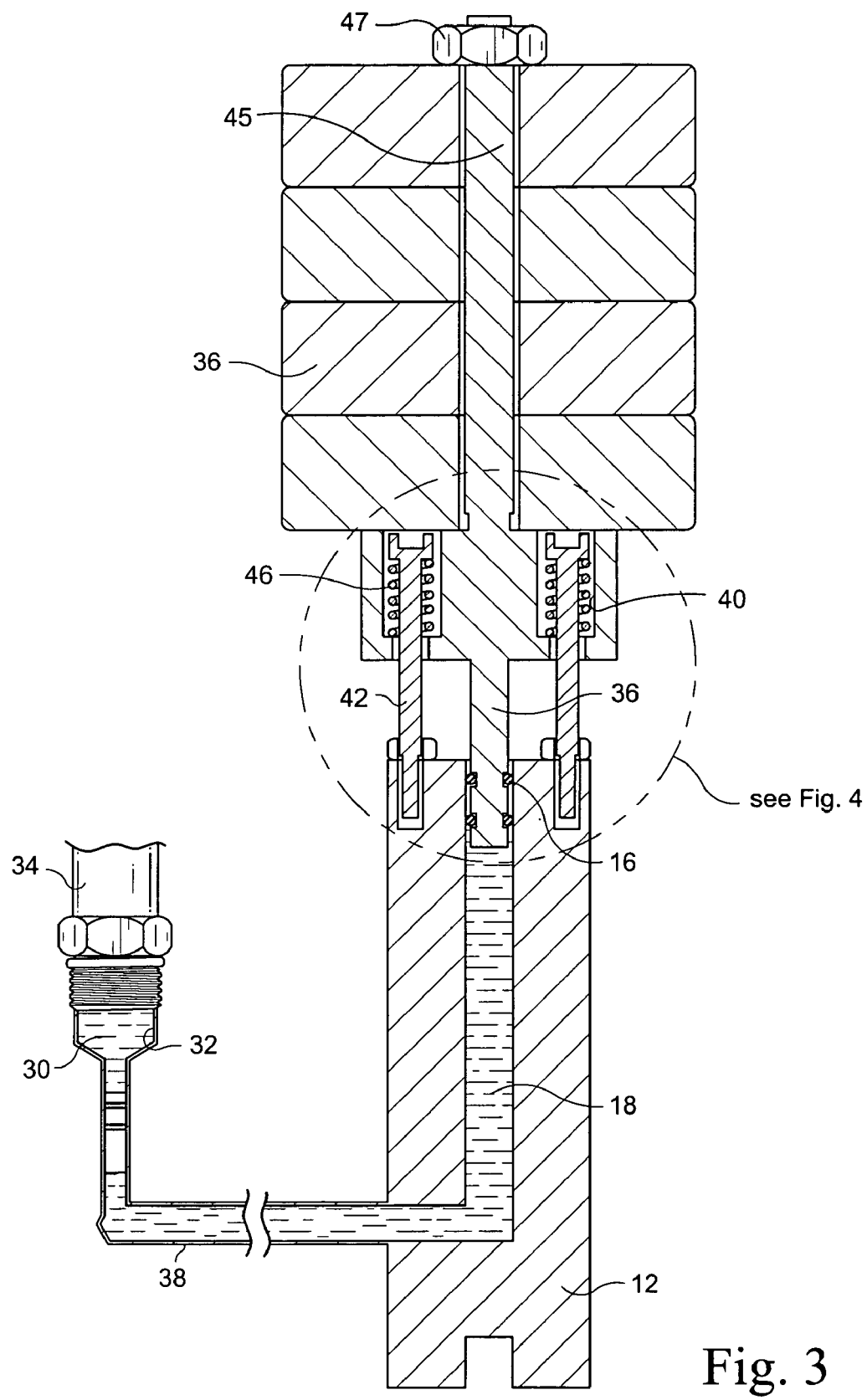
FIG. 3 is a cross-sectional view thereof.
Figure 4:
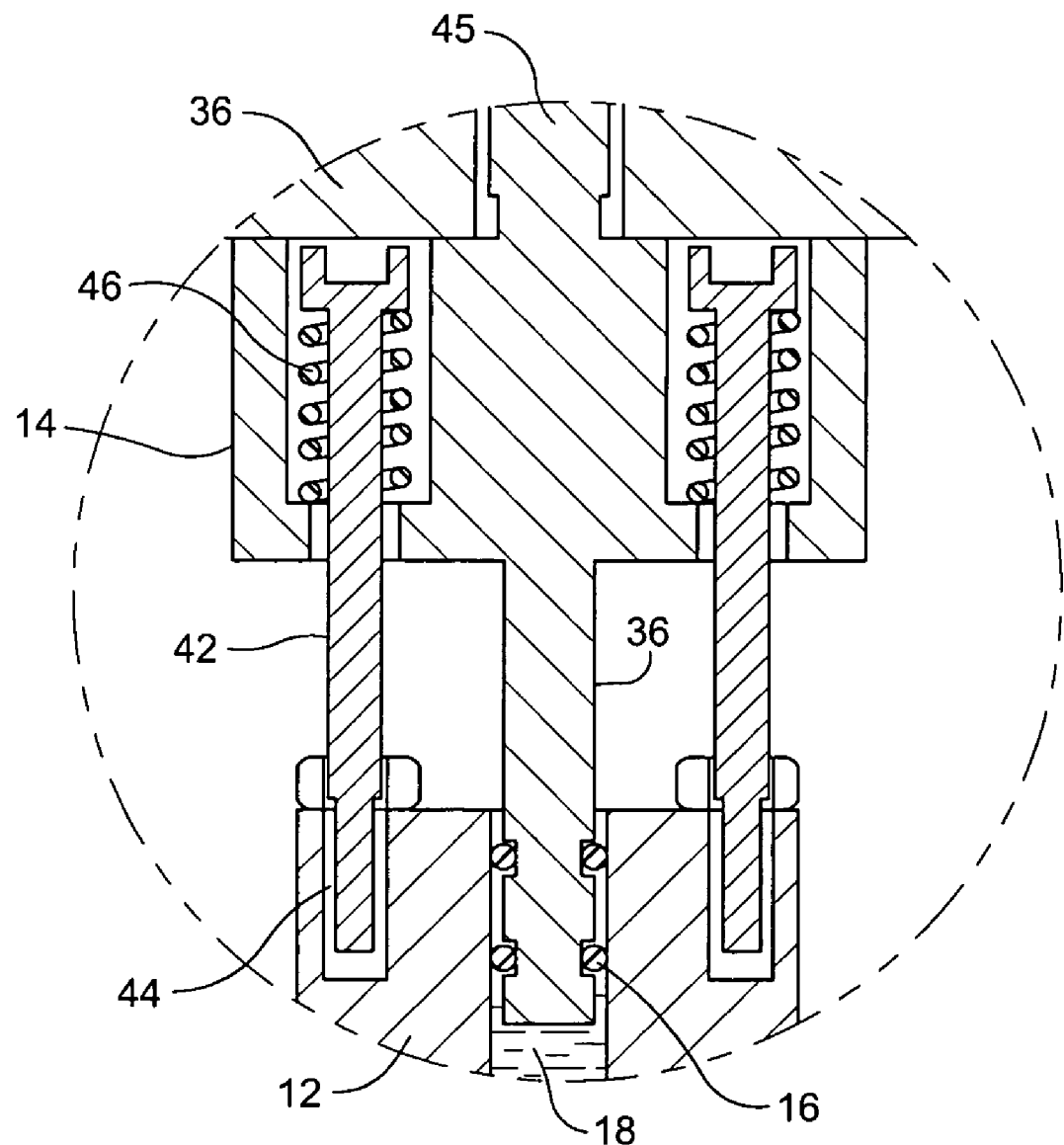
FIG. 4 is an enlarged cross-sectional view of a portion of the testing apparatus.

Referring now to drawing FIGS. 2–4, there is illustrated a specific preferred embodiment of the present invention. In FIG. 2, the cylinder 12 is illustrated mounted on the shaker table 20. The piston 14 includes an active part, i.e., a lower stem 36 (FIGS. 3 and 4) carrying a pair of seals 16, the stem and seals being received in the cylinder opening of cylinder 12. The piston 14 also includes a pair of preferably diametrically opposite openings 40 which receive piston screws 42. The screws 42 are received in the openings 40 and thread into female threaded openings 44 in cylinder 12. Springs 46 (FIGS. 3 and 4) are also disposed in the piston 14 between flanges on their lower ends and the first weight 36 of a plurality of weights. The screws 42 and springs 46 serve to secure the piston 14 to the cylinder 12, while, at the same time, allowing the piston to vibrate in response to the shaker table. The weights 36 may be secured on a stem 45 which projects upwardly from the piston 14 by means of a threaded nut 46. The fluid 18 in the cylinder 12 also communicates via a semi-rigid line 38 with the housing 22. The housing 22 includes a cylinder chamber which receives the piston 26 suitably sealed in the chamber by O-ring seals 28. Additionally, the upper portion of housing 22 has female threads 50 for threaded engagement with a portion of the article 34, e.g., the pressure transducer, for securing the transducers to the testing apparatus. It will be appreciated that the article 34 has a sensing face, not shown, which is exposed to the fluid in the chamber 32.

The operation is similar to the operation previously described with respect to the diagrammatic illustration of FIG. 1. The selected one or more of weights 36 serve in part to generate dynamic pressure in accordance with the equation $p=ma/A$ where p is the pressure generated, m is the mass of the weights and piston, a is the acceleration response to the vibration and A is the surface area of piston 14 in contact with fluid 18. The generated pressure pulses are transmitted to the piston 26 and hence to the second fluid 30, e.g., the caustic or corrosive fluid. The transmitted pressure pulses are thus applied to the sensing face of the article 32. In this preferred embodiment, it will be appreciated that the piston cylinder diameters and weights can be changed as desired to generate desired pressures. For example, a pressure range of 20–200 p.s.i. with the fixture being operated between 100 and 400 Hz, and preferably at about 300 Hz to obtain a resonant frequency, enables the testing apparatus to apply over one billion pressure cycles over a limited time period of two or three weeks to a pressure transducer 32 undergoing testing. More specifically, for example, pressure swings from 20–200 p.s.i. can be generated, with the system vibrating at resonance at 300 Hz, by utilizing 2 pounds-mass of weights and a piston area of 0.1 square inch and an acceleration due to the vibration of 10 g's. At 300 Hz, continuous operation, 1 billion cycles can be achieved in under 40 days. Thus, it will be appreciated that the testing apparatus is operable over a wide range of pressures, can be used at any required temperature subject only to temperature limitations of the materials of the testing apparatus. The testing apparatus may accommodate most fluid media capable of transmitting pressure waves and is particularly useful for testing articles which will be subjected to caustic or corrosive fluids and at a wide range of pressures and frequencies.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:
1. Apparatus for dynamically pressure testing an article comprising:
   a first cylinder containing a first fluid;
   a first piston in contact with the first fluid and movable within said first cylinder;
   a shaker table mounting said first cylinder and said first piston for vibrating the first cylinder and first piston and generating pressure pulses in said first fluid;
   a second fluid cylinder in communication with said first fluid, said second cylinder and a second piston movably carried by said second cylinder being mounted independently of said shaker table, said second piston in contact with the first fluid on one side thereof enabling the generated pressure pulses to vibrate said second piston; and
   a second fluid in said second cylinder in contact with said second piston on an opposite side thereof from said one side for receiving pressure pulses generated by the vibratory movement of said second piston and transmitting the second pressure pulses to an article undergoing dynamic pressure testing in contact with the second fluid.

2. Apparatus according to claim 1 including a weight of predetermined magnitude mounted on said first piston.

3. Apparatus according to claim 1 including a plurality of independent weights for selective mounting on said first piston to alter the magnitude of the generated pressure pulses.

4. Apparatus according to claim 1 wherein said second fluid is a caustic or corrosive fluid and said second piston includes seals for sealing said first and second fluids from one another.

5. Apparatus according to claim 1 wherein said second cylinder includes means for mounting the article thereto.

6. Apparatus according to claim 1 including at least one rod secured to said first cylinder and a spring cooperable between said rod and said piston to enable relative vibration between said first piston and said first cylinder.

7. Apparatus for dynamically pressure testing an article comprising:
   a first cylinder containing a first fluid;
   a first piston in contact with the first fluid and movable within said first cylinder;
   means for vibrating said first cylinder and said first piston to generate pressure pulses in said first fluid;
   a second fluid cylinder in communication with said first fluid, said second cylinder and a second piston movably carried by said second cylinder being mounted independently of said vibrating means, said second piston in contact with the first fluid on one side thereof, enabling the generated pressure pulses to vibrate said second piston; and
   a second fluid in said second cylinder in contact with said second piston on an opposite side thereof from said one side for receiving pressure pulses generated by the vibratory movement of said second piston and transmitting the second pressure pulses to an article undergoing dynamic pressure testing in contact with the second fluid.

8. Apparatus according to claim 7 including a weight of predetermined magnitude mounted on said first piston.

9. Apparatus according to claim 7 including a plurality of independent weights for selective mounting on said first piston to alter the magnitude of the generated pressure pulses.

10. Apparatus according to claim 7 wherein said second fluid is a caustic or corrosive fluid and said second piston includes seals for sealing said first and second fluids from one another.

11. Apparatus according to claim 7 wherein said second cylinder includes means for mounting the article thereto.

12. Apparatus according to claim 7 including at least one rod secured to said first cylinder and a spring cooperable between said rod and said piston to enable relative vibration between said first piston and said first cylinder.

13. A method for dynamically pressure testing an article comprising the steps of:
   providing a first weighted piston and a first cylinder with a first fluid in contact with said piston;
   vibrating said first piston and said first cylinder to generate pressure pulses in said first fluid;
   transmitting the pressure pulses of said first fluid to a second piston mounted in a housing fixed against vibratory movement to vibrate said second piston in response thereto; and
   fixing the article to said housing with said article in contact with a second fluid responsive to vibratory movement of said second piston to transmit pressure pulses to said article.

14. A method according to claim 13 including providing a caustic or corrosive second fluid.

15. A method according to claim 13 including selectively varying the magnitude of the pressure pulses acting on said second piston.

16. A method according to claim 13 including selectively applying a plurality of weights to said first piston to vary the magnitude of the pressure pulses of the first fluid on the second piston.

17. A method according to claim 13 including providing seals about the second piston to seal the first and second fluids from one another.

* * * * *